(12) United States Patent
Payor

(10) Patent No.: US 8,773,947 B2
(45) Date of Patent: Jul. 8, 2014

(54) INSTRUMENTATION PROBE FOR IN SITU MEASUREMENT AND TESTING OF SEABED

(75) Inventor: Stephen David Payor, Bass Hill (AU)

(73) Assignee: Benthic Geotech, Pty Ltd, New South Wales (AU)

( * ) Notice: Subject to any disclaimer, the term of this patent is extended or adjusted under 35 U.S.C. 154(b) by 1591 days.

(21) Appl. No.: 11/813,243

(22) PCT Filed: Nov. 21, 2005

(86) PCT No.: PCT/AU2005/001766
§ 371 (c)(1),
(2), (4) Date: Mar. 12, 2008

(87) PCT Pub. No.: WO2006/076758
PCT Pub. Date: Jul. 27, 2006

(65) Prior Publication Data
US 2008/0257636 A1 Oct. 23, 2008

(30) Foreign Application Priority Data
Jan. 18, 2005 (AU) .................. 2005900193

(51) Int. Cl.
*G01V 1/38* (2006.01)
(52) U.S. Cl.
USPC .................... 367/15; 181/101; 73/866.5
(58) Field of Classification Search
CPC ..................................................... G01N 33/24
USPC ............ 73/153, 726, 152.01, 170.2, 170.32;
114/293; 181/105; 200/61.71;
340/274 R, 282, 547, 686.6, 854.4,
340/854.9, 855.4; 367/35, 57, 81, 83, 134,
367/82; 381/71.1, 94.1, 94.7; 175/39, 40,
175/50; 324/348; 435/9, 287.1; 436/28, 29,
436/151
See application file for complete search history.

(56) References Cited

U.S. PATENT DOCUMENTS 3,906,434 A * 9/1975 Lamel et al. .................... 367/82
3,975,723 A * 8/1976 Bowling et al. ............... 340/547
(Continued)

FOREIGN PATENT DOCUMENTS

NL 1010459 C 5/2000
WO WO 03/056132 7/2003

OTHER PUBLICATIONS

WS Atkins Consultants Ltd, Risk implications in site characterisation and analysis for offshore engineering and design, Health & Safety Executive, 2004, 116 pgs, United Kingdom.

*Primary Examiner* — Isam Alsomiri
*Assistant Examiner* — Daniel L Murphy
(74) *Attorney, Agent, or Firm* — King & Schickli, PLLC

(57) ABSTRACT

A probe assembly (1) suitable for use with apparatus for use in the investigation and/or analysis of an underwater floor of a body of water such as, for example, a seabed. The apparatus includes a depth penetration device (10), and an underwater floor testing tool (11, 12). The probe assembly (1) includes a first coupling for operatively connecting the probe to the depth penetration device (10) and a second coupling for operatively connecting the probe assembly (1) to the underwater floor testing tool (11, 12). The probe assembly (1) further includes a signal processing module (5) for processing information from the tool, a data transmission module (2) for the transmission of data from the signal processing module (5), a power source (3) for operating the data transmission module (2) and the signal processing module (5) and a switch module (4) for selectively connecting from the power source (3) to the data transmission module (2) and signal processing module (5).

21 Claims, 5 Drawing Sheets

(56) References Cited

U.S. PATENT DOCUMENTS

| | | | |
|---|---|---|---|
| 5,439,800 A * | 8/1995 | Thompson | 435/9 |
| 5,737,433 A * | 4/1998 | Gardner | 381/94.7 |
| 5,970,901 A | 10/1999 | Bruce | |
| 6,208,586 B1 * | 3/2001 | Rorden et al. | 367/35 |
| 6,320,820 B1 * | 11/2001 | Gardner et al. | 367/81 |
| 6,343,649 B1 | 2/2002 | Beck et al. | |
| 6,359,569 B2 | 3/2002 | Beck et al. | |
| 6,481,505 B2 | 11/2002 | Beck et al. | |
| 6,526,818 B1 * | 3/2003 | Head et al. | 73/152.01 |
| 6,588,505 B2 | 7/2003 | Beck et al. | |
| 6,856,578 B2 * | 2/2005 | Magine et al. | 367/134 |

\* cited by examiner

INSTRUMENTATION PROBE FOR IN SITU MEASUREMENT AND TESTING OF SEABED

FIELD OF THE INVENTION

The present invention relates to a method and apparatus for investigating soil properties of an underwater floor of a body of water such as for example a seabed.

BACKGROUND OF THE INVENTION

Determining geotechnical, geophysical and geochemical properties of the seabed is an essential part of site assessment for offshore exploration and construction projects such as oil and gasfield platforms, anchorages, pipe and cable laying, wind energy and marine current turbine towers. Soil properties profoundly influence the design and performance of foundations for seabed structures, while detection of shallow gas is important for geohazard assessment during seabed operations or for hydrocarbons exploration potential of a site.

Soil properties are commonly measured using seabed penetrometers, deployed by various means including 'wireline' drillstring, coiled tubes, anchored seabed frames and remotely operated seabed platforms. Different types of apparatus are used according to the type of soil properties being investigated, for example the standard cone penetrometer test is suited for medium to high strength soils, the ball penetrometer for soft soils and the vane shear test and T-bar test for measurement of cohesive soils. In the case of geochemical measurements, sensing apparatus is currently used only above the seafloor via a towed submersible or a remotely operated vehicle, or via wireline deployment from a surface vessel into a borehole. Scientific investigation of the seabed often requires a wide range of instrumentation sensors to be deployed into a borehole. Increasingly, there is a trend for such seabed investigations to be performed at greater depth, in deep and ultra-deep water.

In situ seabed measurement apparatus commonly relies on wired electrical connections between the downhole probe and the seabed equipment or surface vessel for power supply and for data transmission to provide real time analysis and display. In deep water situations, such wireline systems are often deployed from relatively large drillships, floating platforms or dedicated survey vessels, all of which are expensive to operate. Some cheaper methods deploying 'over-the-side' apparatus are known, in which the seabed equipment is powered by a hydraulic umbilical or a battery pack, however these tend to have limited capability in their operating water depth or seabed penetration depth. Moreover, each type of measurement apparatus is currently used as a dedicated single-purpose device, with the disadvantage of little commonality in hardware and handling requirements.

It would thus be advantageous to provide a 'universal' instrumentation probe (UIP) of standardised configuration to which a variety of in situ measurement devices can be connected interchangeably. Such a UIP device would desirably transmit measurement data signals in real time as well as provide in situ data logging and means for remotely retrieving the logged data.

The advent of portable remotely operated seabed platforms with multi-use drilling, sampling, testing and measurement capabilities offers the flexibility to carry a range of in situ probes that can be deployed quickly and interchangeably according to geotechnical needs. However, such platforms that rely on remote makeup of a drillstring from individual lengths of pipe cannot use a wired electrical connection to the downhole apparatus. In this case the downhole apparatus is remotely powered by an attached battery pack.

A known alternative method of data transmission provides wireless communication via acoustic telemetry from the downhole apparatus. The electrical output signal from the measurement probe is converted to an acoustic signal which is transmitted through the drillstring to a receiving microphone coupled to the top of the drillstring. Down-hole acoustic telemetry presently operates only in one direction, from the probe to the seabed apparatus and not vice versa.

In current practice, probes and transmitters are switched on at the surface, at the launch of a deployment, and have no means to be remotely switched off or on. This is a severe disadvantage, as there is insufficient battery capacity to power the apparatus continuously for long deployment cycles, particularly in deepwater operations. Moreover, the built-in data logger may not have sufficient memory to avoid loss of data. In an overall deployment period extending possibly for days, a particular probe may only need to be powered up for short intervals. There is ample battery and memory capacity if the probe could be remotely switched on only when needed for taking in situ measurements. It would be further advantageous therefore to provide remote switching means to power the UIP on and off only as required.

Present acoustic methods of data transmission require a microphone to be coupled to the top of the drillstring. This is achieved simply by sandwiching the microphone housing between the end of the drill pipe and the feed chuck or anvil while applying downward force. With this method it is only possible to receive transmitted data during downward thrusting of the apparatus. In some instances however, such as measuring remoulded soil strength with a ball penetrometer, it would be advantageous also to receive data during upward movement of the apparatus. In other instances it would be advantageous to hold the drillstring in the feed chuck while taking measurements, for example to prevent possible runaway of a long drillstring under its own weight in very soft soils or to rotate a vane shear tool. This is not currently possible and requires the use of an auxiliary friction clamp.

To retrieve logged data in current practice it is necessary to bring the seabed probe assembly back to the surface, disassemble the probe and physically connect the memory module to an interface device for downloading. This can place inconvenient limitations on seabed operations and introduce significant delays in data recovery and verification.

It is the object of the present invention to provide means for alleviating one or more of the aforementioned disadvantages.

According to one aspect of the present invention there is provided a probe assembly suitable for use with apparatus for use in the investigation and/or analysis of an underwater floor of a body of water such as for example a seabed, the apparatus including a depth penetration device and an underwater floor testing tool, the probe assembly including a first coupling for operatively connecting the probe assembly to the depth penetration device and a second coupling for operatively connecting the probe assembly to the underwater floor testing tool, the probe assembly further including a signal processing module for processing information from the tool, a data transmission module for the transmission of data from the signal processing module, a power source for operating the data transmission module and the signal processing module and a switch module for selectively connecting from the power source to the data transmission module and signal processing module. The signal processing module may include an electronics module for processing signals from the tool into data and a data logging module for storing the data. The transmitter module may include an acoustic transmitter.

Preferably the switch module is a remotely actuatable device arranged to electrically connect and disconnect the power source to the processing module and transmitter module. The switch module may include a magnetic responsive switching device responsive to a magnetic field.

The probe assembly may further include a close range wireless communications device.

According to another aspect of the present invention there is provided apparatus for use in the investigation and/or analysis of an underwater floor of a body of water, the apparatus including a depth penetration device, a floor testing tool and a probe assembly as described above, the probe assembly being operatively connected to the depth penetration device and the tool, the apparatus further including a receiving microphone at an end of the depth penetrating device remote from the probe assembly and being acoustically coupled thereto via the depth penetrating device.

The receiving microphone may be contained in a liquid-filled enclosure which is pressure-equalised to the ambient water pressure at the seafloor. The receiving microphone may further be enclosed in a drive unit associated with the depth penetrating device.

According to yet another aspect of the invention there is provided a remotely activatable switch device suitable for use with a probe assembly as described above, the switch device including a switch element arranged in an electric circuit which includes two terminals, one being connectable to the power source and the other being connectable to the signal processing module and data processing module, the switch element being normally caused to adopt one of either a closed position in which the circuit is closed or an open position in which the circuit is opened, the switch being responsive to a magnetic field when in the vicinity thereof to cause the switch to adopt the open position.

The device may include a magnetically transparent housing, an electrically insulated switch body disposed within the housing, the switch element including a reed switch which is movable between the open and closed positions. The magnetic field comprises a magnet assembly mounted in the region of the underwater floor.

In a preferred form of the present invention there is provided a universal instrument probe assembly (UIP) including a remotely operated switch module, a battery power pack module, data conditioning, logging and transmitting modules, in combination with a range of seabed soil testing tools. The UIP is adapted to be connected to a drillstring or similar soil penetrating means, remotely deployed from seabed apparatus.

The UIP assembly may include a standard 36 mm diameter cylindrical housing. At the upper end it can be joined to similar sized extension rods or to a drill pipe adapter. The upper end of the UIP may also contain a transmitter which is capable of sending an acoustic data signal a distance of at least 100 m through an attached drill pipe. Attached below the acoustic transmitter module is a battery power pack module and a remotely operated switch module. The switch module may be electrically connected in series with the battery power pack and allows the transmitter and probe electronics to be powered on and off as required.

In one form, the switch module may include a magnetic switch wired in a 'normally-closed' position and arranged in a housing of magnetically transparent material such that the switch operates to an 'open' position when in proximity to a strong external magnetic field. The external magnetic field may be provided for example by rare earth permanent magnets located in a separate structure up to 200 mm laterally distant from the UIP switch module. When the switch module is assembled to the adjacent parts of the UIP, it is hermetically sealed against ambient water pressure to its rated depth.

The UIP assembly may also include a data logging module and an electronics module attached in series with the switch module. The electronics module may be electrically terminated with a multi-pin connector and can also be assembled onto an extension tube. The lower end of the extension tube may be adapted to attach a soil measurement tool, such as a cone penetrometer, a ball penetrometer, a vane shear tool or a gas sensor. A multi-core cable and matching connector inside the extension tube may be provided in order to link the electronics module to the soil measurement device, to supply power to the device and obtain measurement data signals. All connectors may be of underwater type suitable for the rated depth of the UIP assembly.

The length of the extension tube may be adapted according to the length of the particular type of attached soil testing device. In this way the overall length of the UIP tool assembly may be standardised to suit a single means of tool storage and robotic handling on the seabed platform. A variety of soil testing tools may thus be carried ready for deployment interchangeably, according to the soil conditions encountered.

In some applications such as, for example when used with a downhole gas sensor probe, it may be advantageous to connect drilling fluid or flushing water to the measurement probe. For this purpose the extension tube is of larger diameter than the UIP and may attach directly to the drill pipe adapter near the upper end of the UIP instead of to the electronics module at the lower end of the UIP. The extension tube thus encloses the UIP over its length with a small radial clearance to form an annular passage. Through this passage flushing water may be pumped from the drillstring to the sensor at the lower end of the extension tube.

In a further variation the UIP assembly may include an outer protection tube which normally encloses the vanes of a vane shear tool attachment but retracts when the vane tool is pushed into cohesive soil.

According to one example of the method of use of the invention, prior to launch from the surface vessel the seabed platform is prepared with a range of in situ testing and measurement tools, each assembled to a UIP. Typically the tool assemblies are stored systematically in a rack or magazine from which they can be remotely selected and deployed into a borehole via a robotic loading mechanism. The storage magazine is provided with permanent magnets located in proximity to the switch modules that are part of the UIP.

In the presence of the strong magnetic field the switch in a tool assembly is held in the open state and the tool remains powered down. The tool is powered up only while it is removed from the magazine for individual downhole use, when the switch reverts to the closed state in the absence of the strong magnetic field. In this way battery energy is drained only while the tool is being actively used, otherwise there may be insufficient battery capacity to last the full duration of a seabed operations cycle.

Whenever the UIP is powered up the measurement signals from the attached probe are processed by the electronics module into a digital data stream which is logged into the memory module. With the tool assembly attached to the drillstring the data stream is transmitted wirelessly from the borehole to the seabed platform by means of the acoustic transmitter in the UIP and the receiving microphone coupled to the top of the drillstring. From the seabed platform the data stream is further conveyed in real time to an operator on the surface vessel via electrically wired, fibre optic or other suitable means.

In a further aspect of the invention the UIP memory module may include a wireless communications device and an aerial or alternatively an electromagnetically transparent window, sealed to withstand hydrostatic pressures in a deepsea environment and allowing radio or magnetic signals to be transmitted and received. It is well known that radio signals are rapidly attenuated in seawater and that undersea radio communication is not practical over much distance. However it is possible to transmit over short distances (tens of millimeters). Magnetic induction communications is another suitable wireless technology for close range underwater data transfer. In this case a radiating coil transmits a magnetic field, with typical data rates up to 200 kbits/s. Therefore by fixing a similar communications device to the seabed apparatus in a position where the memory module may be brought into close proximity by a robotic tool handling mechanism, it is possible to establish two-way data transfer.

A number suitable wireless communications protocols exist, including those based on the IEEE802.11 standards, operating in the ISM (Industrial Scientific Medical) band at 2.4 GHz. These include proprietary protocols known under trademarks such as Bluetooth and AirPort, which commonly support data rates to 54 Mbit/s. The fixed communications device on the seabed apparatus may be connected by electrical wiring, optical fibre or by a combination of means to a surface operating station. Data downloading may thus be accomplished remotely from the UIP memory module while on the seabed. Alternatively if the UIP is brought to the surface, wireless downloading may be quickly accomplished using conventional communications-enabled computer equipment.

According to a further aspect of the invention there is provided an improved microphone configuration which allows the acoustic data signal to be received during both downward and upward movement of the drillstring in the seabed drilling platform. The drillstring water seal in the rotation unit and chuck assembly is adapted to include a microphone assembly in a separate chamber, while providing a path for the drilling fluid to pass to the drillstring.

The water seal may comprise a hollow shaft arranged to seal at the lower end into the top of the drill pipe while the drill pipe is gripped in the rotary chuck. The water seal shaft may pass up through a rotation drive unit to a rotary seal, commonly referred to as a water coupling or water swivel. The water coupling provides a non-rotating connection point for drilling fluid to be pumped via the water seal shaft through the rotation unit to the drillstring.

A small diameter connecting tube may pass from the microphone chamber through the bore of the water seal shaft and extends through the water coupling. The connecting tube encloses a wire that carries the output signal from the microphone to a single-contact rotary joint at the top of the water coupling. The microphone chamber, connecting tube and rotary joint are fully oil filled and pressure balanced to ambient conditions via connection to an external pressure compensator.

The microphone assembly may include a face plate with attached piezo crystals and resonant mass. The face plate cam forms the lower element of the water seal assembly and includes a spigot which aligns and acoustically couples the water seal assembly to the top face of the drill pipe.

To provide required acoustic coupling sensitivity the microphone face plate is preferably decoupled from the large mass of the rotation unit by means of a resilient compression washer placed between the face plate and the attachment flange of the rotation unit.

For operation of the enclosed microphone, the face plate is pressed in firm contact with the drillstring by applying downward force (bit weight) with the drill string held by a fixed lower clamp. The resilient washer is compressed axially and can be locked in this state by actuating the rotary chuck to grip the top of the drillstring. The compression force in the resilient washer thus holds the microphone face plate in contact with the top of the drillstring regardless of upward or downward movement of the drillstring in the borehole. Movement of the drillstring is positively restrained at all times either by the rotary chuck or the fixed rod clamp.

In addition to receiving measurement data from the UIP tool assembly during soil testing operations, the built-in microphone may also allow an operator to remotely 'listen' to rotary drilling operations on the seabed, thus providing another source of information for interpretation and control of the cutting process.

Thus the present invention may provide for real time data transmission during downward, upward and rotational movement of the soil testing apparatus.

Preferred embodiments of the invention will be hereinbefore described with reference to the accompanying drawings, and in those drawings:

LIST OF FIGURES

DESCRIPTION OF EXAMPLE EMBODIMENTS OF THE INVENTION

Figure 1:
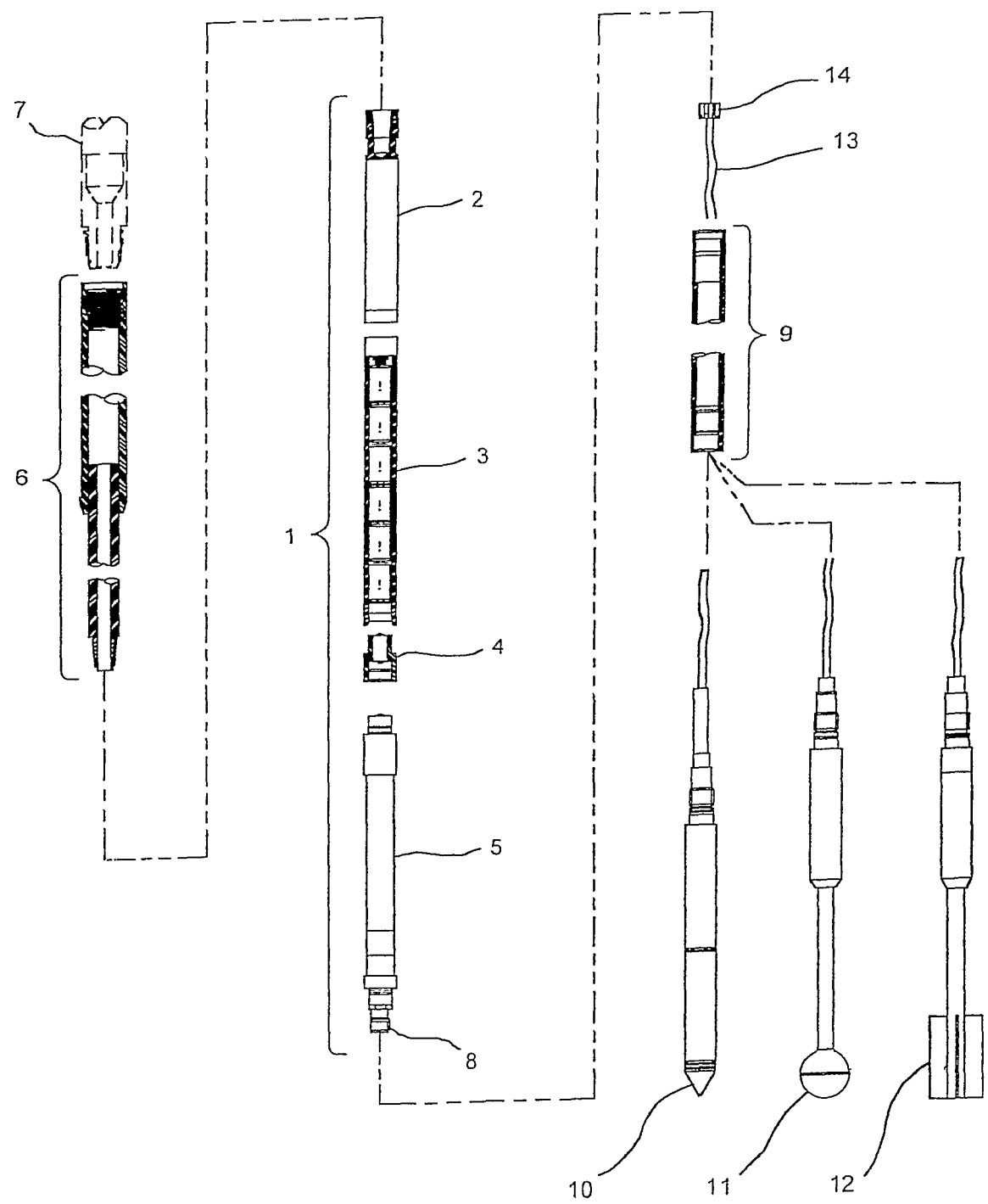
FIG. 1 illustrates an expanded and partly cross-sectioned view of the universal instrument probe (UIP) with examples of soil testing attachments.

With reference to FIG. 1 a universal instrument probe (UIP) is provided as an assembly 1 which includes in sequence from top to bottom: an acoustic transmitter module 2; a battery power pack module 3; a switch module 4; and an electronics module 5 for signal conditioning and data logging. Transmitter module 2 has means for joining its upper end to an adapter rod 6, which connects to a drillstring 7 or similar soil penetrating apparatus.

Electronics module 5 is electrically terminated with a multi-pin connector 8 and may be further assembled onto an extension tube 9. The lower end of extension tube 9 is adapted to attach a soil measurement tool, such as a cone penetrometer 10, ball penetrometer 11, or vane shear tool 12. A multi-core connecting cable 13 and matching plug 14 inside extension tube 9 link electronics module 5 to the attached soil measurement probe, to supply power to the probe and receive measurement data signals. To facilitate assembly of the soil measurement probe to UIP assembly without twisting connecting cable 13, extension tube 9 is preferably provided with a right-handed thread at one end and a left-handed thread at the opposite end. Connectors 8 and 14 and cable assembly 13 are of underwater type suitable for the rated operating depth of UIP assembly 1.

UIP assembly 1 is preferably in the form of a standard 36 mm diameter cylindrical housing. A number of the modules are of a conventional type or adaptations of existing products for deepwater operation, including acoustic transmitter module 2, battery power pack module 3 and electronics module 5, which form part of a cordless Cone Penetrometer Test system manufactured by Geotech AB.

The length of adapter rod 6 and/or extension tube 9 may be configured if necessary according to the length of the particular type of attached soil testing probe. In this way the overall length of the UIP and probe assembly may be standardised to suit a single means of tool storage and robotic handling on the seabed platform.

Figure 2:
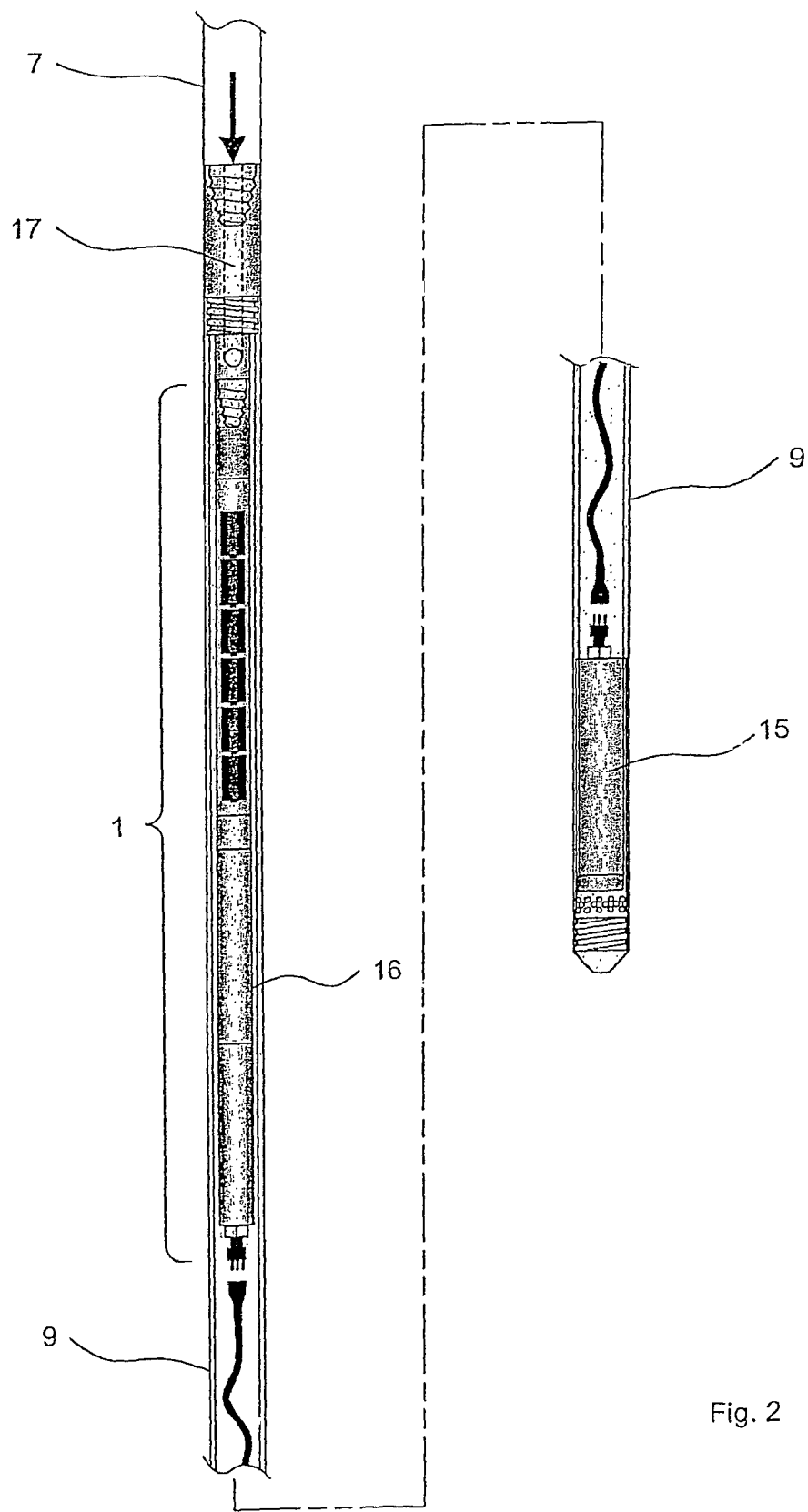
FIG. 2 illustrates the UIP in an enclosed extension tube configuration with gas probe attachment.

With reference to FIG. 2 showing a further embodiment, extension tube 9 attaches directly to adapter rod 6. In this configuration extension tube 9 encloses UIP assembly 1 and at the lower end is adapted to attach alternative measurement tools such as a gas sensor 15. The inner diameter of extension tube 9 is larger than the outer diameter of UIP assembly 1, forming an annular passage 16. Drilling fluid or flushing water may flow through extension tube 9 from drillstring 7, via interconnecting passages 17 in adapter 6 and through annular passage 16, to discharge at the lower end of extension tube 9 in the vicinity of sensor 15.

Figure 3:
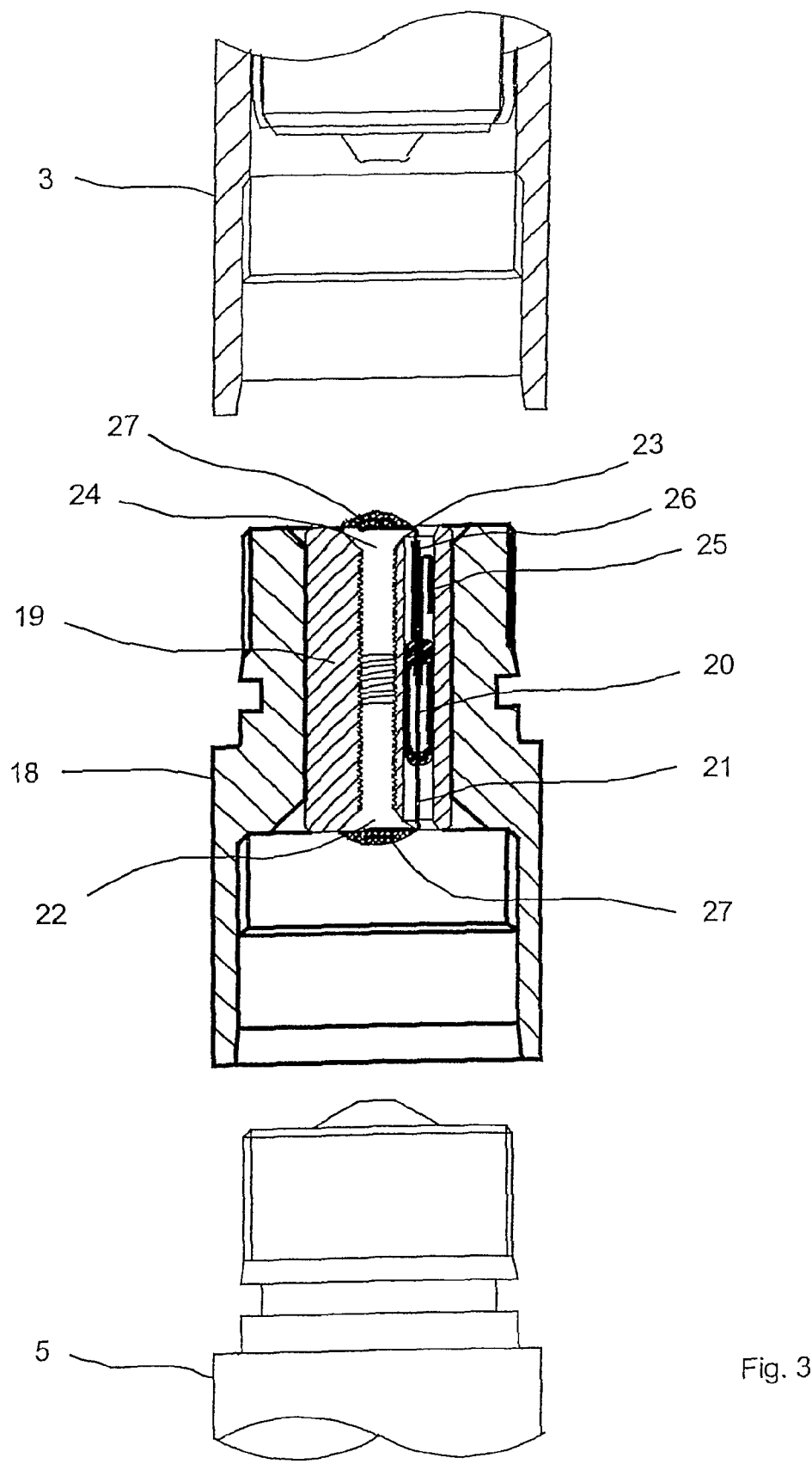
FIG. 3 illustrates the UIP magnetic switch module in cross-section.

With reference to FIG. 3, switch module 4 includes a structural housing 18 constructed from a magnetically transparent material, preferably a high strength stainless alloy such as 'Nitronic 50', with end features adapted for sealed connection to battery housing 3 and electronics module 5. A switch body 19, constructed of electrically insulating material, for example glass-filled PTFE, is contained loosely and located concentrically in housing 18. Switch body 19 has a through hole parallel to but offset from the axis of symmetry in which is located a glass reed switch 20, such as Assemtech Europe product number 8602-0551-020. The common lead 21 of reed switch 20 is connected to a common terminal 22 positioned centrally in one end of switch body 19. At the opposite end of switch body 19 the normally-closed lead 23 of reed switch 20 is connected to a normally-closed terminal 24, also positioned centrally. The normally-open lead 25 of reed switch 20 remains unconnected and is folded back on itself to act as a magnetic antenna. An insulating sleeve 26 separates the pair of switch leads. A solder button 27 preferably joins leads 21 and 23 to terminals 22 and 24 respectively, forming suitable electrical contacts to mate with battery pack 3 and electronics module 5.

In a variation of switch module 4, switch body 19 may be made to standard dimensions of a dry cell battery. In this case the switch assembly may be substituted for one of the batteries that are arranged in series in power supply module 3, provided the casing of power supply module 3 is constructed of non-magnetic material.

Figure 4:
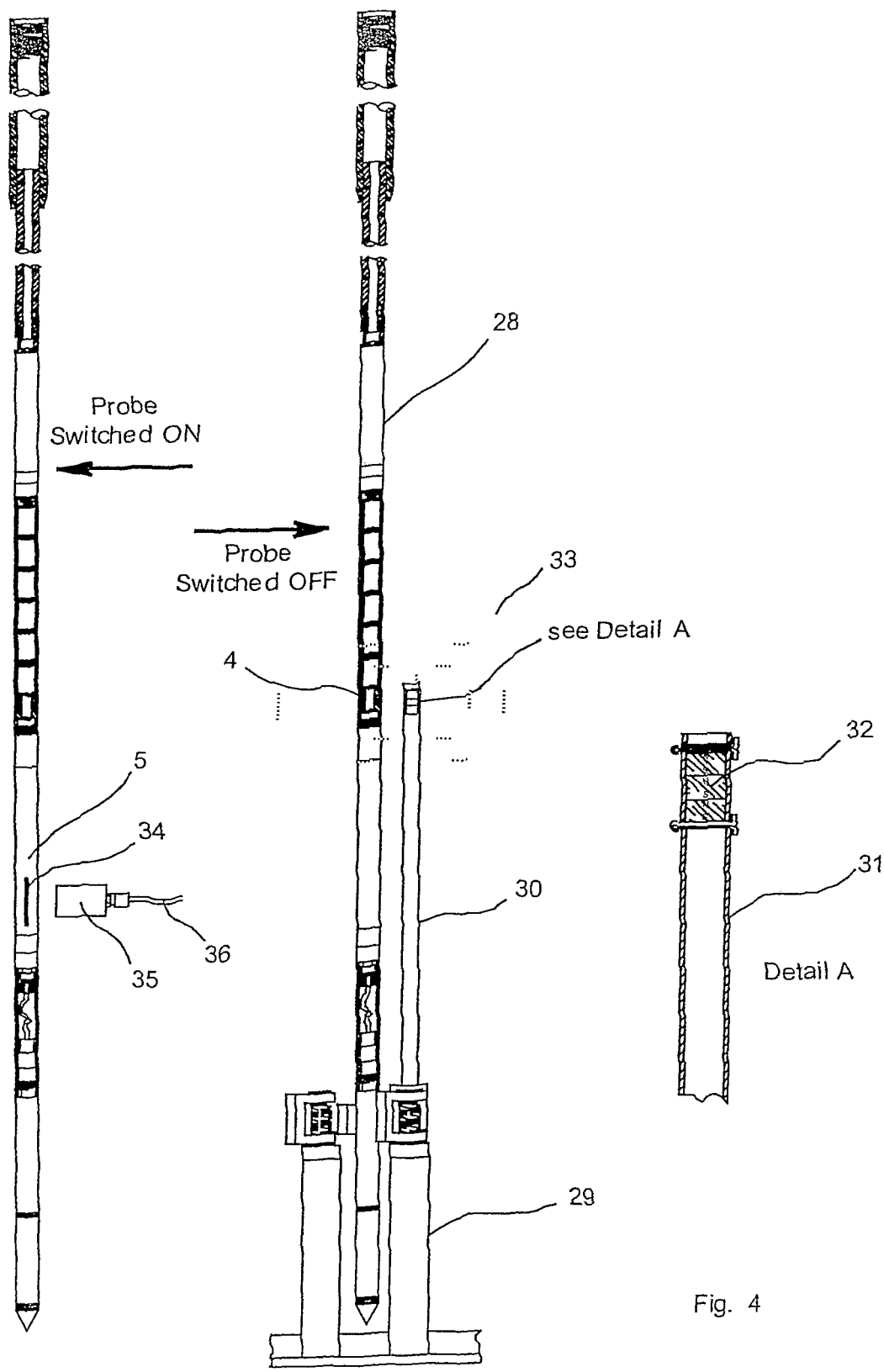
FIG. 4 illustrates the means of remote switching of the UIP power supply and wireless data download from the memory module.

FIG. 4 illustrates a preferred manner of remote power switching in the UIP. A tool assembly 28 containing UIP assembly 1 is normally held in a tool rack or magazine 29 which is provided with a magnet assembly 30. Magnet assembly 30 includes a non-magnetic casing 31 and a number of rare earth permanent magnets 32, positioned to create a strong magnetic field 33 in proximity to UIP switch module 4. A single magnet assembly 30 may be used to operate multiple adjacent tool assemblies. Magnets may be grouped at different heights in casing 31 to accommodate different positions of switch module 4 in tool assembly 28. While switch module 4 in tool assembly 28 remains in proximity to magnet assembly 30, switch module 4 remains magnetically actuated in the open state. Battery power pack 3 is thus electrically isolated and transmitter module 2 and electronics module 5 remain de-energised.

With further reference to FIG. 4, electronics module 5 includes a first internal radio frequency communications device that is connected electrically to an external antenna 34. Antenna 34 is sealed in an outer groove on the housing of module 5 such that it is substantially protected against damage. A second radio communications device 35 is provided in a fixed position on the seabed apparatus where electronics module 5 may be brought into close proximity by a robotic tool handling mechanism. Wireless two-way data transfer is thus established between the first radio communications device in module 5 and second radio communications device 35, and further via a wired or optical link 36 to a, remote operator station on the surface vessel.

Prior to deployment of the seabed equipment from the surface vessel, each tool assembly 28 is charged with a fresh set of batteries in power supply module 3 and is manually loaded into tool magazine 29. At the seabed a selected tool assembly 28 may be removed under robotic control from magazine 29 for downhole operations, and when so removed from magnetic field 33, switch module 4 reverts to the normally closed state and energises transmitter module 2 and electronics module 5. Once tool assembly 28 is returned to magazine 29 power is again switched off, thus conserving sufficient battery energy for multiple tool use during an extended seabed deployment. Whenever UIP assembly 1 is energised, a data stream from the attached soil measurement tool is transmitted acoustically by transmitter module 2. The acoustic data signal travels up the drillstring to a receiving microphone which converts it back to an electrical signal. The data stream is also electronically logged in module 5 and may be downloaded via communications device 35 before tool assembly 28 is replaced in magazine 29.

Figure 5:
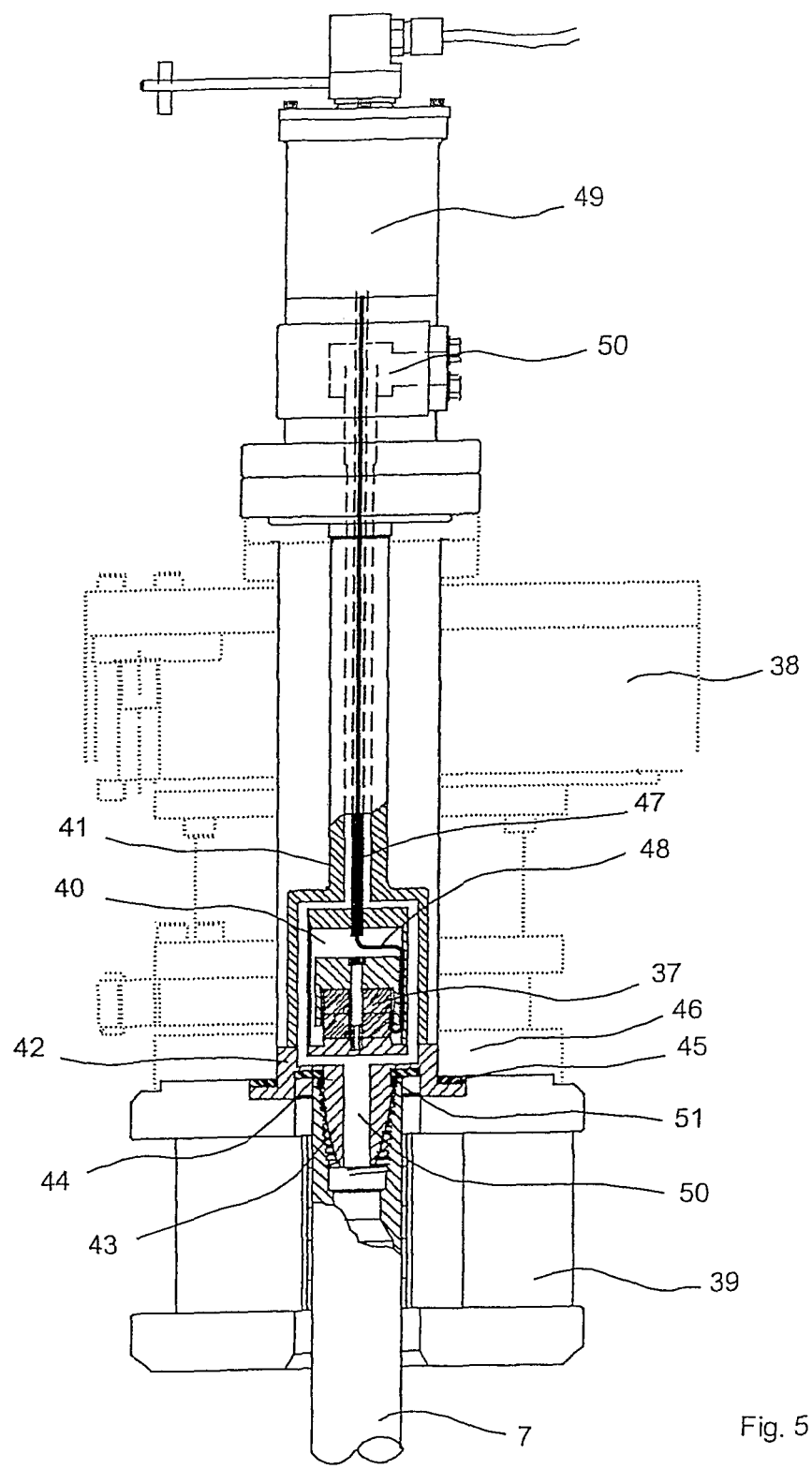
FIG. 5 shows a schematic arrangement of the enclosed receiving microphone in the rotary drive unit.

With reference to FIG. 5 a further aspect of the invention provides a piezo-electric microphone assembly 37 enclosed in the top drive unit 38 which lowers, rotates and elevates drillstring 7 via a chuck 39. Microphone assembly 37 occupies a separate chamber 40 within the water seal shaft assembly 41 which passes through the centre of drive unit 38. A microphone face plate 42 forms the lower element of water seal shaft assembly 41 and includes a spigot 43 which aligns and acoustically couples microphone assembly 41 to the upper end 44 of drillstring 7. A resilient compression washer 45 is positioned between face plate 42 and the attachment flange 46 of drive unit 38.

A small-diameter connecting tube 47 extends from microphone chamber 40 through the bore of water seal shaft assembly 41. Connecting tube 47 encloses a wire 48 from microphone 37 to a single-contact rotary joint 49 attached at the top of water seal shaft assembly 41. Connecting tube 47 is peripherally sealed at the entry to chamber 40 and to rotary joint 49. Chamber 40, connecting tube 47 and rotary joint 49 are oil filled and pressure balanced to ambient conditions via connection to an external pressure compensator.

Water seal shaft assembly 41, face plate 42 and spigot 43 are provided with interconnecting passages 50 which allow drilling fluid to be supplied under pressure from an external pump into drillstring 7. An o-ring seal 51 prevents fluid leakage at the joint between spigot 43 and drillstring 7.

For operation of the enclosed microphone assembly 37, face plate 42 is pressed in firm contact with drillstring 7 by applying downward force (bit weight) with top drive unit 38 while drillstring 7 is axially restrained by a fixed lower clamp. Resilient washer 45 is compressed axially and is locked in this state by actuating rotary chuck 39 to grip the top of drillstring 7. The compression force in resilient washer 45 thus holds face plate 42 and drillstring 7 in contact, regardless of upward or downward movement of drillstring 7. The measurement data stream from the downhole probe assembly is transmitted acoustically through drillstring 7 and received by microphone assembly 37. The electrical output signal from microphone 37 is carried by wire 48 through rotary joint 49 and subsequently transmitted in real time to an operating station on the surface vessel.

The reference to any prior art in this specification is not, and should not be taken as, an acknowledgment or any form of suggestion that that prior art forms part of the common general knowledge in Australia.

Throughout the specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

Finally, it is to be understood that the inventive concept in any of its aspects can be incorporated in many different constructions so that the generality of the preceding description is not to be superseded by the particularity of the attached drawings. Various alterations, modifications and/or additions may be incorporated into the various constructions and arrangements of parts without departing from the spirit or ambit of the invention.

The invention claimed is:

1. An apparatus for in situ geotechnical measurement of an underwater bed of a body of water, the apparatus comprising:
   a seabed platform which in use is disposed on the underwater bed;
   a depth penetration device which comprises a drillstring;
   an underwater bed testing tool which in use is received within a borehole in the underwater bed; and
   a probe assembly which in use is received within the borehole in the underwater bed, comprising:
      a first coupling for operatively connecting the probe assembly to the depth penetration device;
      a second coupling for operatively connecting the probe assembly to the underwater bed testing tool; and
      a plurality of modules which in use are assembled together and configured so that the plurality of modules can be received within the borehole, the plurality of modules including a signal processing module for processing information received from the underwater bed testing tool, a data transmission module for the wireless transmission of data through the drillstring from the signal processing module to the seabed platform, and a power source module for powering the data transmission module, the signal processing module and the underwater bed testing tool, the plurality of modules further comprising a switch module which includes a switch device which can electrically connect and disconnect the power source module to the data transmission module, the signal processing module and the underwater bed testing tool when the probe assembly is in the region of the seabed platform.

2. The apparatus according to claim 1, wherein the signal processing module includes an electronics module for processing signals from the underwater bed testing tool into data and a data logging module for storing the data.

3. The apparatus according to claim 1, wherein the data transmission module includes an acoustic transmitter for the wireless transmission of an acoustic signal through the drillstring.

4. The apparatus according to claim 3, further including a receiving microphone near an end of the drillstring remote from the probe assembly.

5. The apparatus according to claim 4, wherein the receiving microphone is contained in a liquid-filled enclosure which is pressure-equalized to the ambient water pressure at the underwater bed of the body of water.

6. The apparatus according to claim 5, wherein the receiving microphone is further enclosed in a top drive unit associated with the depth penetrating device.

7. The apparatus according to claim 4, wherein the receiving microphone is aligned and acoustically coupled to an upper end of the drillstring.

8. The apparatus according to claim 1, wherein the probe assembly includes a wireless communications device for electromagnetic or magnetic wireless communication between the probe assembly and a further wireless communications device provided as part of the seabed platform.

9. The apparatus according to claim 1, wherein the switch device is a self-actuating switch device.

10. The apparatus according to claim 9, wherein the switch device switches responsive to an external magnetic field to electrically connect or disconnect the power source module.

11. The apparatus according to claim 10, wherein the switch device self-actuates depending on proximity of the switch device to a source of the external magnetic field.

12. The apparatus according to claim 1, wherein the switch device includes a switch element arranged in an electric circuit which includes a first terminal connectable to the power source module and a second terminal connectable to the signal processing module, the data processing module, and the underwater bed testing tool, the switch element being normally caused to adopt a position in which power is supplied to the signal processing module, the data transmission module, and the underwater bed testing tool, the switch being responsive to a magnetic field when in the vicinity thereof to cause the switch to adopt a different position in which power is not supplied to the signal processing module, the data transmission module, and the underwater bed testing tool, the magnetic field being generated in the region of the seabed platform.

13. The apparatus according to claim 12, wherein the switch module includes a magnetically transparent housing, an electrically insulated switch body disposed within the magnetically transparent housing, and the switch element includes a reed switch which is movable between an open position and a closed position.

14. The apparatus according to claim 12, wherein the magnetic field is generated by a magnet assembly operatively mounted to the seabed platform.

15. The apparatus according to claim 1, wherein the signal processing module, the power source module and the data transmission module are arranged end to end, with the first coupling and the second coupling being at respective opposite ends of the probe assembly.

16. The apparatus according to claim 15, wherein the data transmission module is at the end adjacent the first coupling and the signal processing module is at the end adjacent the second coupling.

17. The apparatus according to claim 1, wherein in use the drillstring is a variable length of interconnected drill pipes.

18. The apparatus according to claim 1, wherein the probe assembly is covered by an extension tube that provides an annular passage between an outer surface of the probe assembly and an inner surface of the extension tube.

19. The apparatus according to claim 18, wherein the extension tube is connected at one end to the underwater bed testing tool.

20. The apparatus according to claim 1, wherein the power source module is positioned between the switch module and the data transmission module, and the switch module is positioned between the power source module and the signal processing module.

21. An apparatus for in situ geotechnical measurement of an underwater bed of a body of water via a borehole formed in the underwater bed, the apparatus comprising:
- a seabed platform for positioning on the underwater bed;
- a depth penetration device comprising a drillstring;
- an underwater bed testing tool for positioning within the borehole; and
- a probe assembly for positioning within the borehole, comprising:
    - a first coupling for operatively connecting the probe assembly to the depth penetration device;
    - a second coupling for operatively connecting the probe assembly to the underwater bed testing tool; and
    - a plurality of modules for positioning within the borehole, the plurality of modules including a signal processing module for processing information received from the underwater bed testing tool, a data transmission module for the wireless transmission of data through the drillstring from the signal processing module to the seabed platform, and a power source module for powering the data transmission module, the signal processing module and the underwater bed testing tool, the plurality of modules further comprising a switch module including a switch for electrically connecting and disconnecting the power source module to the data transmission module, the signal processing module and the underwater bed testing tool, including when the probe assembly is in the region of the seabed platform.

* * * * *